United States Patent
Sandberg et al.

(10) Patent No.: US 12,247,137 B2
(45) Date of Patent: Mar. 11, 2025

(54) RENEWABLE, HIGHLY ISOPARAFFINIC DISTILLATE FOR SOLVENT USE

(71) Applicant: Neste Oyj, Espoo (FI)

(72) Inventors: Kati Sandberg, Porvoo (FI); Virpi Rämö, Porvoo (FI); Jenni Nortio, Porvoo (FI); Anna Karvo, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 16/958,802

(22) PCT Filed: Dec. 20, 2018

(86) PCT No.: PCT/EP2018/086111
§ 371 (c)(1),
(2) Date: Jun. 29, 2020

(87) PCT Pub. No.: WO2019/129625
PCT Pub. Date: Jul. 4, 2019

(65) Prior Publication Data
US 2021/0062015 A1 Mar. 4, 2021

(30) Foreign Application Priority Data
Dec. 29, 2017 (FI) .................. 20176190

(51) Int. Cl.
| | | |
|---|---|---|
| *C09D 7/20* | (2018.01) | |
| *C10G 3/00* | (2006.01) | |
| *C10G 45/58* | (2006.01) | |
| *C10L 1/08* | (2006.01) | |

(52) U.S. Cl.
CPC ............ *C09D 7/20* (2018.01); *C10G 3/50* (2013.01); *C10G 45/58* (2013.01); *C10L 1/08* (2013.01); *C10G 2300/1007* (2013.01); *C10G 2300/1014* (2013.01); *C10G 2300/1018* (2013.01); *C10G 2300/301* (2013.01); *C10G 2300/4018* (2013.01); *C10G 2400/08* (2013.01); *C10G 2400/18* (2013.01); *C10L 2200/043* (2013.01); *C10L 2200/0469* (2013.01); *C10L 2200/0484* (2013.01); *C10L 2270/04* (2013.01)

(58) Field of Classification Search
CPC .... C10G 2300/1007; C10G 2300/1014; C10G 2300/1018; C10G 2300/301; C10G 2300/304; C10G 2300/4018; C10G 2400/08; C10G 2400/18; C10G 3/50; C10G 45/58; C10G 65/043; C10L 1/08; C10L 2200/043; C10L 2200/0469; C10L 2200/0484; C10L 2270/04; Y02E 50/10; Y02P 30/20

See application file for complete search history.

(56) References Cited

U.S. PATENT DOCUMENTS

| | | |
|---|---|---|
| 2008/0244962 A1 | 10/2008 | Abhari et al. |
| 2011/0178261 A1* | 7/2011 | Feher .................. C07C 7/04 |
| | | 526/340.2 |
| 2013/0109893 A1* | 5/2013 | Robota ................ C10G 67/04 |
| | | 585/734 |
| 2015/0191404 A1* | 7/2015 | Aalto .................. C10G 45/58 |
| | | 585/16 |
| 2017/0009144 A1 | 1/2017 | Aalto et al. |
| 2018/0148656 A1 | 5/2018 | Germanaud et al. |

FOREIGN PATENT DOCUMENTS

| | | | |
|---|---|---|---|
| EP | 0876444 A1 | 11/1998 | |
| EP | 2368967 A1 | 9/2011 | |
| EP | 3095838 A1 * | 11/2016 | ............ C10G 3/42 |
| EP | 3095844 A1 | 11/2016 | |
| JP | 2011526640 A | 10/2011 | |
| JP | 2017503855 A | 2/2017 | |
| JP | 2018519374 A | 7/2018 | |
| WO | 2015101837 A2 | 7/2015 | |
| WO | 2017198905 A1 | 11/2017 | |

OTHER PUBLICATIONS

Edwards, et al., U.S. Air Force Hydroprocessed Renewable Jet (HRJ) Fuel Research—Jul. 2012 Interim Report, Jan. 8, 2013, 92 pages.
International Search Report (PCT/ISA/210) issued on Feb. 22, 2019, by the European Patent Office as the International Searching Authority for International Application No. PCT/EP2018/086111.
Office Actions (4) dated Apr. 19, 2018; Sep. 3, 2018; Dec. 5, 2019; and Feb. 3, 2020.
Written Opinion (PCT/ISA/237) issued on Feb. 22, 2019 by the European Patent Office as the International Searching Authority for International Application No. PCT/EP2018/086111.
Office Action (Notice of Reasons for Refusal) issued on Sep. 20, 2022, by the Japanese Patent Office in corresponding Japanese Patent Application No. 2020-536621, and an English Translation of the Office Action. (9 pages).
Office Action issued on Sep. 21, 2022, by the Chinese Patent Office in corresponding Chinese Patent Application No. 201880080053.5, and a machine English Translation of the Office Action. (10 pages).
Office Action issued on Feb. 16, 2024, by the Canadian Patent Office in corresponding Canadian Patent Application No. 3,084,707. (4 pages).

* cited by examiner

*Primary Examiner* — Latosha Hines
(74) *Attorney, Agent, or Firm* — Buchanan Ingersoll & Rooney PC

(57) ABSTRACT

A renewable solvent composition having a high i-paraffin content of at least 91.0 wt.-% and a boiling in a range of from 150° C. to 260° C. is disclosed. The solvent composition can provide a good balance between solvency power and cold properties and is usable in a broad application field.

18 Claims, No Drawings

RENEWABLE, HIGHLY ISOPARAFFINIC DISTILLATE FOR SOLVENT USE

TECHNICAL FIELD

The present invention relates to a renewable, highly isoparaffinic (i-paraffinic) solvent composition, to its use and to a method of its manufacture.

TECHNICAL BACKGROUND

There is a trend in solvents use in moving towards less VOC (volatile organic carbon) intensive and safer alternatives and a further trend to substitute well-established fossil solvent compositions by solvent compositions which are obtained from a renewable raw material (renewable solvent compositions). However, in the prior art, it was found to be difficult to achieve favourable overall solvent properties, such as good cold properties and high solvency power with renewable solvent compositions.

EP 876444 A1 describes a high purity solvent composition which comprises a mixture of C8 to C20 n-paraffins and i-paraffins boiling in the range 320° F. to 650° F.

WO 2015/101837 A1 relates to a paraffinic solvent composition mainly consisting of C14 and C15 paraffins.

However, the balance between solvency power and cold properties in these solvent compositions still leaves room for improvement.

SUMMARY OF THE INVENTION

The present invention is defined in the independent claims. Further beneficial embodiments are set forth in the dependent claims. Specifically, the present invention relates to one or more of the following items:

1. A solvent composition comprising 91.0 wt.-% or more i-paraffins (iso-paraffins) and having a boiling point in the range of 150° C. to 260° C., wherein the solvent composition is derived from a renewable raw material.
2. The solvent composition according to item 1, which has a boiling point in the range of 160° C. to 250° C., preferably 170° C. to 240° C.
3. The solvent composition according to any one of the preceding items, which comprises more than 50.0 wt.-% dimethylated, trimethylated or higher methylated i-paraffins relative to all i-paraffins in the solvent composition.
4. The solvent composition according to any one of the preceding items, wherein the content of C5 to C16 paraffins is 90 wt.-% or more, preferably 95 wt.-% or more, 96 wt.-% or more, 97 wt.-% or more, 98 wt.-% or more, or 99 wt.-% or more relative to the solvent composition as a whole.
5. The solvent composition according to any one of the preceding items, which has a freezing point of −50° C. or below, preferably −60° C. or below, more preferably −65° C. or below, −68° C. or below, −70° C. or below, or −72° C. or below.
6. The solvent composition according to any one of the preceding items, which has an aniline point of 85° C. or below, preferably 83° C. or below, 81° C. or below, 80° C. or below, 79° C. or below, or 78° C. or below.
7. The solvent composition according to any one of the preceding items, which has an Kauri-butanol (KB) number of 21.5 or higher, preferably 22.0 or higher, 23.0 or higher, 24.0 or higher, 25.0 or higher, 26.0 or higher or 27.0 or higher.
8. The solvent composition according to any one of the preceding items, wherein content of i-paraffins in the solvent composition is 92.0 wt.-% or higher, preferably 93.0 wt.-% or higher, more preferably 94.0 wt.-% or higher, 95.0 wt.-% or higher, 96.0 wt.-% or higher, 97.0 wt.-% or higher, 97.5 wt.-% or higher, or 98.0 wt.-% or higher.
9. The solvent composition according to any one of the preceding items, wherein content of i-paraffins in the solvent composition is 100 wt.-% or lower, preferably 99.8 wt.-% or lower, 99.5 wt.-% or lower, 99.2 wt.-% or lower, or 99.0 wt.-% or lower.
10. The solvent composition according to any one of the preceding item, which comprises more than 55.0 wt.-%, preferably more than 60.0 wt.-%, more than 65.0 wt.-% or more than 70.0 wt.-% dimethylated, trimethylated or higher methylated i-paraffins relative to all i-paraffins in the solvent composition.
11. The solvent composition according to any one of the preceding items, wherein the content of C5 to C15 paraffins is 80 wt.-% or more, preferably 85 wt.-% or more, 90 wt.-% or more, 95 wt.-% or more, 96 wt.-% or more, 97 wt.-% or more, 98 wt.-% or more, or 99 wt.-% or more relative to the solvent composition as a whole.
12. The solvent composition according to any one of the preceding items, wherein the content of C5 to C16 i-paraffins is 55 wt.-% or more, preferably 58 wt.-% or more, 60 wt.-% or more, 62 wt.-% or more, 64 wt.-% or more, 65 wt.-% or more, or 66 wt.-% or more relative to all C5 to C16 paraffins in the solvent composition as a whole.
13. The solvent composition according to any one of the preceding items, wherein the content of C5 to C15 i-paraffins is 50 wt.-% or more, preferably 55 wt.-% or more, 58 wt.-% or more, 60 wt.-% or more, 62 wt.-% or more, 64 wt.-% or more, or 65 wt.-% or more relative to all C5 to C15 paraffins in the solvent composition as a whole.
14. A use of the solvent composition according to any one of the preceding items as a solvent in coating, paint, lacquer, varnish, polish, ink, adhesive, sealant, resin, plastic, cleaning composition, pigment dispersion, antioxidant, biocide, insecticide, air freshener, crop protection composition, detergent, grease removal composition, dry cleaning composition, cosmetic, personal care composition, pharmaceutical, dental impression material, vaccine, food ingredient, flavour composition, fragrance, natural oil extraction, oil field chemical, drilling mud composition, extraction process composition, plasticizer for elastomer, paper processing chemical, lubricant, functional fluid, transformer oil, metal working composition, rolling or cutting fluid, water treatment composition, wood treatment composition, construction chemical, mould release material, explosive, mining chemical, or a combination thereof.
15. The use according to item 14, wherein the solvent composition is used as a solvent in a paint.
16. The use according to item 14, wherein the solvent composition is used as a solvent in a coating.
17. A method for producing a solvent composition according to any one of items 1 to 13, the method comprising the steps of:
  (i) providing a renewable raw material;
  (ii) hydrotreating and/or isomerising the renewable raw material to provide a isomeric raw material;
  (iii) distilling the isomeric raw material, thereby obtaining a fraction boiling in the range of 150° C. to 260° C., preferably in the range of 160° C. to 250° C., and most preferably in the range of 170° C. to 240° C., which is recovered as the solvent composition, optionally after further purification.
18. The method according to item 17, wherein the renewable raw material is a wax, a fat or an oil.

19. The method according to item 17 or 18, wherein the renewable raw material is a fat or an oil of plant origin (including algae and fungi), of animal origin (including fish) or of microbial origin, in particular vegetable oil/fat, animal oil/fat, waste oil/fat from the food industry, algae oil/fat and/or microbial oil, such as palm oil, rapeseed oil, algae oil, jatropha oil, soybean oil, cooking oil, vegetable oil, animal fat and/or fish fat.

20. The method according to any one of items 17 to 19, wherein the step (ii) of hydrotreating and/or isomerising is carried out under conditions optimized for the production of jet fuel.

21. The method according to any one of items 17 to 20, wherein the step (ii) of hydrotreating and/or isomerising includes a step (ii-1) of hydrotreating the renewable raw material and a step (ii-2) of isomerising the hydrotreated material obtained in the hydrotreating step (ii-1).

22. The method according to any one of items 17 to 21, wherein isomerising is carried out in a process comprising an isomerisation stage and a re-isomerisation stage.

DETAILED DESCRIPTION OF THE INVENTION

The invention is now explained in detail with reference to specific embodiments. It is to be noted that any feature of the embodiments may be combined with any feature of another embodiment provided that such a combination does not result in a contradiction.

The present invention relates to a solvent composition comprising 91.0 wt.-% or more i-paraffins and having a boiling point in the range of 150° C. to 260° C., wherein the solvent composition is derived from a renewable raw material. It is preferable that the solvent composition has a boiling point (boiling start point) of 160° C. or more, more preferably of 170° C. or more. It is preferable that the solvent composition has a boiling point (boiling end point) of 250° C. or less, more preferably of 240° C. or less. The boiling point is particularly preferably in the range of 160° C. to 250° C., more preferably 170° C. to 240° C.

The inventors of the present invention found that a fraction having excellent solvent properties and low boiling point but nevertheless moderate vapour pressure at room temperature can be obtained from a highly-isomerised biological raw material. The solvent composition of the present invention furthermore provides good cold properties while having relatively low volatility. Boiling points/temperatures and boiling ranges in the present invention refer to boiling temperatures/ranges under atmospheric pressure (1 atm, 1013 mbar), unless specified otherwise.

Solvent fractions obtained from a biological raw material in known production lines usually have a high boiling point of more than 260° C. and/or the isomerisation degree of these low boiling fractions is rather low. The present invention is based on the finding that a solvent fraction boiling from 150° C. to 260° C. and having a high i-paraffin content can be extracted from renewable material in considerable yield. Specifically, it was surprisingly found that the relative content of iso-alkanes in the low boiling point range is remarkably high when the production process is optimized for production of jet-grade fuel. The solvent composition of the present invention can thus be extracted from this production line in good yields.

In the present invention, the expressions "boiling in a range of xxx° C. to yyy° C.", "having a boiling point/boiling temperature in the range of xxx° C. to yyy° C." each mean that the material (composition) has a boiling start point of xxx° C. and a boiling end point of yyy° C. Boiling points may be determined according to EN ISO 3405 method.

In the present invention, i-paraffins (iso-paraffins) are isomeric paraffins, i.e. paraffins having at least one branch in the carbon chain. On the other hand, n-paraffins (normal paraffins) are paraffins having a linear carbon chain, i.e. without branching (but including optionally cyclic paraffins having no branches). Paraffins within the meaning of the present invention are saturated hydrocarbon compounds (consisting of carbon atoms and hydrogen atoms), which may be cyclic (monocyclic, di-cyclic, etc.) but is preferably non-cyclic. If not otherwise specified, the term paraffin includes both n-paraffin and i-paraffin.

The solvent composition of the present invention contains 91.0 wt.-% or more i-paraffins (relative to the composition as a whole taken as 100%). The i-paraffin content can be determined using a suitable method, for example gas chromatography (GC). The n-paraffinic and i-paraffinic component distribution can be identified by gas chromatography using FID detector. Area-% of hydrocarbons in the FID-chromatogram is equal to wt.-% of the component. The components are identified based on model compound (n-paraffins) chromatograms. The limit of quantitation for individual components is 0.01 wt.-%. The solvent composition of the present invention is a liquid composition, and it preferably has a boiling point in the range of 160° C. to 250° C., more preferably 170° C. to 240° C.

The content of i-paraffins in the solvent composition may be 94.0 wt.-% or higher, 95.0 wt.-% or higher, 96.0 wt.-% or higher, 97.0 wt.-% or higher, 97.5 wt.-% or higher, or 98.0 wt.-% or higher.

The solvent composition preferably comprises more than 50.0 wt.-% dimethylated, trimethylated or higher methylated i-paraffins relative to all i-paraffins in the solvent composition. The content of dimethylated, trimethylated or higher methylated i-paraffins relative to all i-paraffins in the solvent composition is in particular preferably more than 55.0 wt.-%, more than 60.0 wt.-%, more than 65.0 wt.-% or more than 70.0 wt.-%.

The inventors found that the properties of the solvent composition are improved as the i-paraffin content increases. In particular, cold properties can be significantly improved with increased methyl branching degree.

Further, the inventors found that such a composition having a high i-paraffin content, and in particular having a high degree of methyl branching, can be produced from biological raw material with high yield. In the present invention, di methylated, trimethylated or higher methylated i-paraffins refer to i-paraffins having two, three or more methyl branches, respectively, or briefly said more than one methyl-branch in the carbon chain.

The content of C5 to C16 paraffins in the solvent composition is preferably 90 wt.-% or more relative to the solvent composition as a whole (taken as 100%). The content of C5 to C16 paraffins may be 92 wt.-% or more, 93 wt.-% or more, 94 wt.-% or more, 95 wt.-% or more or 96 wt.-% or more. The paraffin content can be determined using any suitable method, e.g. gas chromatography.

Having a content of C5 to C16 paraffins (i.e. paraffins having 5 to 16 carbon atoms) within this range provides a good balance between boiling point and vapour pressure of the composition and furthermore provides good cold properties. As already said above, paraffins in this context refers to both n-paraffins and i-paraffins.

The content of C5 to C15 paraffins in the solvent composition is preferably 80 wt.-% or more relative to the solvent composition as a whole (taken as 100%). The content of C5 to C15 paraffins may be 85 wt.-% or more, 90 wt.-% or more, 92 wt.-% or more, 93 wt.-% or more, 94 wt.-% or more, 95 wt.-% or more or 96 wt.-% or more. The paraffin content can be determined using any suitable method, e.g. gas chromatography.

Having a high content of C5 to C15 paraffins further improves solvent properties.

The solvent composition preferably has a freezing point of −50° C. or below or −60° C. or below. The freezing point may further be −65° C. or below, −68° C. or below, −70° C. or below, or −72° C. or below. Usually, the freezing point will be −100° C. or higher, and may be −90° C. or higher. The freezing point may be determined in accordance with IP 529:2015.

The solvent composition preferably has an aniline point of 85° C. or below. The aniline point may further be 84° C. or below, preferably 83° C. or below, 81° C. or below, 80° C. or below, 79° C. or below, or 78° C. or below. The aniline point may be determined in accordance with ISO 2977: 1997. The lower aniline point of a solvent is, the better solubility properties it has and thus better usability in different applications since e.g. stability of additives in the blend is improved.

The solvent composition preferably has a Kauri-butanol (KB) number of 21.5 or higher. The KB number may further be 22.0 or higher, preferably 23.0 or higher, 24.0 or higher, 25.0 or higher, 26.0 or higher or 27.0 or higher. The KB number may be determined in accordance with ASTM D 1133:2013. Higher KB number means better solvent power, i.e. solvent dissolves certain materials better.

In the solvent composition of the present invention, it is preferable that the content of i-paraffins (relative to the whole of the solvent composition) be 94.0 wt.-% or higher, 95.0 wt.-% or higher, 96.0 wt.-% or higher, 97.0 wt.-% or higher, 97.5 wt.-% or higher, or 98.0 wt.-% or higher. Generally, the i-paraffin content may be 100 wt.-% (i.e. the composition consists of i-paraffins) but the content is usually lower and may be 99.8 wt.-% or lower, 99.5 wt.-% or lower, 99.3 wt.-% or lower, 99.2 wt.-% or lower, 99.1 wt.-% or lower, or 99.0 wt.-% or lower.

The higher the content of i-paraffins, the better solvent properties (in particular cold properties) can be expected. However, since obtaining very high i-paraffin contents is usually more challenging, achieving 100% i-paraffin content is usually not efficient from an economic point of view.

It is further preferable that the content of C5 to C16 paraffins be 95 wt.-% or more relative to the solvent composition as a whole. The content may further preferably be 96 wt.-% or more, 97 wt.-% or more, 98 wt.-% or more, or 99 wt.-% or more. The inventors of the present invention surprisingly found that i-paraffins in the C5 to C16 range show excellent solvent properties, in particular a good balance between solvency power and cold properties.

In the solvent composition of the present intention, the content of C5 to C16 i-paraffins is preferably 55 wt.-% or more, more preferably 58 wt.-% or more, 60 wt.-% or more, 62 wt.-% or more, 64 wt.-% or more, 65 wt.-% or more, or 66 wt.-% or more relative to all C5 to C16 paraffins in the solvent composition as a whole. The higher the i-paraffins content in the C5 to C16 range (relative to all paraffins in the C5 to C16 range), the better are the cold properties of the solvent composition as a whole.

In the solvent composition of the present intention, the content of C5 to C15 i-paraffins is preferably 50 wt.-% or more, more preferably 55 wt.-% or more, 58 wt.-% or more, 60 wt.-% or more, 62 wt.-% or more, 64 wt.-% or more, or 65 wt.-% or more relative to all C5 to C15 paraffins in the solvent composition as a whole. Cold properties of the solvent composition can be further improved within this range.

Thanks to its favourable composition and good balance between cold properties and solvency power, the solvent composition of the present invention is applicable to a broad range of applications. In particular, the solvent composition may be employed as a solvent in coating, paint, lacquer, varnish, polish, ink, adhesive, sealant, resin, plastic, cleaning composition, pigment dispersion, antioxidant, biocide, insecticide, air freshener, crop protection composition, detergent, grease removal composition, dry cleaning composition, cosmetic, personal care composition, pharmaceutical, dental impression material, vaccine, food ingredient, flavour composition, fragrance, natural oil extraction, oil field chemical, drilling mud composition, extraction process composition, plasticizer for elastomer, paper processing chemical, lubricant, functional fluid, transformer oil, metal working composition, rolling or cutting fluid, water treatment composition, wood treatment composition, construction chemical, mould release material, explosive, mining chemical, or a combination thereof. Most favourably, the solvent composition can be used as a solvent in a paint or as a solvent in a coating (as a solvent in a coating composition). Although the solvent composition of the present invention can be used as the sole solvent in the above applications, the solvent composition may also be used as a co-solvent, i.e. in combination with one or more other solvents.

The solvent composition of the present invention may be produced by any suitable method as long as the composition is derived from a renewable raw material. A suitable method for producing a solvent composition, which is preferred according to the present invention, comprises the steps of:

(iv) providing a renewable raw material;
(v) hydrotreating and/or isomerising the renewable raw material to provide a isomeric raw material;
(vi) distilling the isomeric raw material, thereby obtaining a fraction boiling in the range of 150° C. to 260° C., preferably 160-250° C., more preferably 170-240° C., which is recovered as the solvent composition, optionally after further purification.

In the present invention, isomerisation (a step of isomerising) includes any method which increases the degree of isomerisation, i.e. which increases the content of carbon chains having a high degree of branching relative to the content of carbon chains having a lower degree of branching. For example, isomerisation may include catalytic isomerisation in the presence of a catalyst and in the presence or absence of hydrogen and may also include cracking.

In the present invention, any renewable raw material may be used as a renewable raw material. For example, the renewable raw material may be a wax, a fat or an oil and may also be free fatty acid(s) (including salts thereof) or fatty acid ester(s).

The renewable raw material is preferably a fat or an oil, more preferably a fat or an oil of plant origin (including algae and fungi), of animal origin (including fish) or of microbial origin, and in particular vegetable oil/fat, animal oil/fat, waste oil/fat from the food industry, algae oil/fat and/or microbial oil, such as palm oil, rapeseed oil, algae oil, jatropha oil, soybean oil, cooking oil, vegetable oil, animal fat and/or fish fat. The renewable raw material may be a mixture of compounds which is derived from a renewable source.

Usually, the renewable raw material comprises heteroatoms (in addition to carbon atoms and hydrogen atoms), the renewable raw material may in particular comprise oxygen atoms. If the renewable raw material comprises heteroatoms, it is preferable that the hydrotreatment is carried out to remove the heteroatoms and to produce a hydrocarbon material, preferably n-paraffins or a mixture of n-paraffins and i-paraffins. The hydrotreatment may also be carried out such that isomerisation is promoted so as to predominantly (more than 50 wt.-% of the hydrocarbon products) produce i-paraffins.

In the method for preparing the solvent composition of the present invention, the step (ii) of hydrotreating and/or isomerising is preferably carried out under conditions optimized for the production of jet fuel. Such conditions are in particular conditions which mainly result in low-boiling (e.g. 130° C.-300° C.) paraffins having a high degree of branching. Various process conditions can be modified to achieve the above, e.g. type and amount (or WHVS) of catalyst in the hydroprocessing and/or isomerisation step, temperature in the hydroprocessing and/or isomerisation step and product post-processing (e.g. partial product recycling or partial optional re-isomerisation of the product).

EXAMPLES

The present invention is further illustrated by way of Examples. However, it is to be noted that the invention is not intended to be limited to the exemplary embodiments presented in the Examples.

Example 1

Palm oil was used as a renewable raw material. The palm oil was subjected to hydrodeoxygenation in a continuous flow fixed bed tube reactor using NiMo as a catalyst and under a pressure of 47 bar, WHSV of 0.5 h$^{-1}$ and at a reaction temperature of 330° C. Hydrogen to oil ratio was 1000 normal litres H$_2$ per litre oil feed (1000 Nl/l). The hydrotreatment product was separated from gaseous components and water to give a liquid organic phase (mainly n-paraffins; also referred to as "oil phase") containing no oxygen compounds.

The oil phase obtained above was subjected to isomerisation in a continuous flow fixed bed tube reactor using Pt-SAPO-catalyst under a pressure of 37 bar, WHSV of 1.3 h$^{-1}$ and at a reaction temperature of 330° C. Hydrogen to oil ratio was 300 normal litres H$_2$ per litre oil feed.

The product obtained from the isomerisation stage (isomeric raw material) was subjected to fractionation (by distillation) to give a solvent composition in accordance with the present invention (yield: about 40 wt.-% of the isomeric raw material) boiling in the range of 170° C. to 260° C. (boiling start point: 170° C.; boiling end point: 260° C.).

Evaluation

Two different feed materials, a highly isomerized renewable material, and a material with isomerization degree of 93 wt.-% and boiling in the range of 170° C.-330° C. were distilled to obtain a solvent product at distillation range 170° C.-240° C. Solvency properties of the composition boiling in the range of 170° C.-240° C. were clearly improved relative to the original feed material. Similarly, a significant improvement is observed compared to the i-paraffinic fraction (boiling in the same range) obtained from the material with 93% isomerization degree.

Aniline points and Kauri-butanol (KB) values were determined in accordance with ISO2977:1997 and ASTMD1133: 2013, respectively, to evaluate the solubility behaviour of the solvents of the present invention. Table 1 summarizes the findings of the experiments.

Aniline point of petroleum products and hydrocarbon solvents describes the minimum equilibrium solution temperature for equal volumes of aniline and sample. Aromatic hydrocarbons having effective solubilizing properties exhibit the lowest, and paraffinic the highest values. The aniline point tends to increase when a molecular weight increases. As visible from Table 1, best aniline point level was obtained when taking the fraction 170° C.-240° C. from a highly i-paraffinic product.

Kauri-Butanol value relates to the determination of the relative solvency power of hydrocarbon solvents used in paint and lacquer formulations. Kauri-butanol value is the volume in millilitres at 25° C. of the solvent, corrected to a defined standard, required to produce a defined degree of turbidity when added to 20 g of a standard solution of kauri resin in normal butyl alcohol. The higher the KB value of the solvent, the better the relative solvency power is.

Table 1 shows that the KB values of the highly i-paraffinic fraction (170° C.-240° C.) is clearly improved relative to the original feed material, and also improved when compared to the i-paraffinic fraction obtained in 5% yield from the NEXBTL process with 93% isomerization degree.

Table 1 summarizes the i-paraffin contents, dimethylated and higher methylation degree components (di+ methylated) from total i-paraffins, aniline points and KB values of the highly i-paraffinic solvent composition boiling in the range of 170° C.-240° C. and a comparison to a reference solvent composition and to feed material properties.

TABLE 1

| | Method | Units | Highly i-paraffinic product 170° C.-330° C. | Highly i-paraffinic fraction 170° C.-240° C. | i-paraffinic product 170° C.-330° C. | i-paraffinic fraction 170° C.-240° C. |
|---|---|---|---|---|---|---|
| i-paraffins | GC method | — | 94 | 91 | 93 | 85 |
| Di + methylated i-paraffins from total i-paraffins | GC method | wt.-% | 57 | 62 | 56 | 46 |
| Aniline point | ISO2977 | ° C. | 93 | 79 | 97 | 83 |
| KB value | ASTMD1133 | — | 21.5 | 27 | 19.5 | 25.5 |

As can be seen from the above-said, the solvent composition of the present invention, which boils within a narrow temperature range and has a high i-paraffin content, is superior over conventional i-paraffinic solvent compositions. Although it is not desired to be bound to theory, it is held that the improved properties of the solvent composition of the present invention are achieved because the high i-paraffinic content in combination with a narrow boiling point range ensures that even the light-boiling components are predominantly present in the form of i-paraffins. That is, it was found that in the i-paraffinic content in conventional i-paraffin solvents, having roughly the same overall i-paraffin content, the i-paraffinic ratio (relative amount of i-paraffins) is more pronounced in the higher-boiling range (corresponding to higher carbon numbers) as compared to the low-boiling rang (corresponding to lower carbon numbers). In other words, the conventional solvent compositions contain a much higher relative amount of n-paraffins having a given low carbon number as compared to the solvent composition of the present invention. It is assumed that the low content of low-carbon number n-paraffins (in particular C5-C10 n-paraffins) in the solvent composition of the present invention is responsible for the good cold properties in combination with good solvency power.

The invention claimed is:

1. A solvent composition, comprising:
    paraffins,
    wherein the paraffins include C5 to C15 paraffins and i-paraffins;
    wherein a content of the C5 to C15 paraffins is 95 wt.-% or more,
    wherein a content of the i-paraffins is 91.0 wt.-% or more, relative to the solvent composition as a whole;
    wherein there is more than 55.0 wt.-% dimethylated, trimethylated or higher methylated i-paraffins relative to all of the i-paraffins in the solvent composition;
    and wherein:
    the solvent composition is a derivation of a renewable raw material including at least one or more of: a fat or an oil of any plant origin, of any animal origin, or of any microbial origin, including algae and fungi, fish, vegetable oil/fat, animal oil/fat, food industry waste oil/fat, algae oil/fat, microbial oil, palm oil, rapeseed oil, algae oil, jatropha oil, soybean oil, cooking oil, vegetable oil, animal fat or fish fat; and
    the solvent composition having a boiling point in a range of 150° C. to 250° C. and an aniline point of 83° C. or below via hydrotreating the renewable raw material to form hydrotreated material, isomerising the hydrotreated material obtained in the hydrotreating of the renewable raw material to provide an isomeric raw material, and distilling the isomeric raw material to form the solvent composition.

2. The solvent composition according to claim 1, wherein the content of C5 to C16 paraffins is 96 wt.-% or more relative to the solvent composition as a whole.

3. The solvent composition according to claim 1, which has at least one of a freezing point of −50° C. or below.

4. The solvent composition according to claim 1, which has an Kauri-butanol (KB) number of 21.5 or higher.

5. The solvent composition according to claim 1, wherein content of i-paraffins in the solvent composition is at least one of 92.0 wt.-% or higher, 93.0 wt.-% or higher, 94.0 wt.-% or higher, 95.0 wt.-% or higher, 96.0 wt.-% or higher, 97.0 wt.-% or higher, 97.5 wt.-% or higher, or 98.0 wt.-% or higher.

6. The solvent composition according to claim 1, comprising:
    more than 60.0 wt.-%, dimethylated, trimethylated or higher methylated i-paraffins relative to all i-paraffins in the solvent composition.

7. The solvent composition according to claim 1, wherein the content of C5 to C16 paraffins is 99 wt.-% or more, relative to the solvent composition as a whole.

8. A method of applying a solvent composition, the solvent composition being the solvent composition of claim 1, the method comprising:
    applying the solvent composition as at least one of a solvent in coating, paint, lacquer, varnish, polish, ink, adhesive, sealant, resin, plastic, cleaning composition, pigment dispersion, antioxidant, biocide, insecticide, air freshener, crop protection composition, detergent, grease removal composition, dry cleaning composition, cosmetic, personal care composition, pharmaceutical, dental impression material, vaccine, food ingredient, flavour composition, fragrance, natural oil extraction, oil field chemical, drilling mud composition, extraction process composition, plasticizer for elastomer, paper processing chemical, lubricant, functional fluid, transformer oil, metal working composition, rolling or cutting fluid, water treatment composition, wood treatment composition, construction chemical, mould release material, explosive, mining chemical, or a combination thereof.

9. A method for producing a solvent composition having 91.0 wt.-% or more i-paraffins, a boiling point in a range of 150° C. to 250° C., and a low content of low-carbon number C5 to C10 n-paraffins relative to the solvent composition as a whole, wherein the solvent composition is a derivation of a renewable raw material, the method comprising:
    (i) providing a renewable raw material, the renewable raw material including at least one or more of: a fat or an oil of any plant origin, of any animal origin, or of any microbial origin, including algae and fungi, fish, vegetable oil/fat, animal oil/fat, food industry waste oil/fat, algae oil/fat, microbial oil, palm oil, rapeseed oil, algae oil, jatropha oil, soybean oil, cooking oil, vegetable oil, animal fat or fish fat;
    (ii) hydrotreating the renewable raw material to form hydrotreated material and isomerising the hydrotreated material obtained in the hydrotreating of the renewable raw material to provide an isomeric raw material; and
    (iii) distilling the isomeric raw material, thereby obtaining a fraction boiling in at least one of a range of 150° C. to 250° C., a range of 160° C. to 250° C., or a range of 170° C. to 240° C., which is recovered as the solvent composition, optionally after further purification;
    wherein the solvent composition comprises
    paraffins, the paraffins including C5 to C15 paraffins and i-paraffins;
    wherein a content of the C5 to C15 paraffins is 95 wt.-% or more and a content of the i-paraffins is 91.0 wt.-% or more relative to the solvent composition as a whole;
    wherein there is more than 55.0 wt.-% dimethylated, trimethylated or higher methylated i-paraffins relative to all of the i-paraffins in the solvent composition and the solvent composition has an aniline point of 83° C. or below.

10. The method according to claim 9, wherein the renewable raw material is a fat or an oil.

11. The method according to claim 9,
    wherein the isomerising of the hydrotreated material includes carrying out isomerising in a process having an isomerisation stage and a re-isomerisation stage, wherein the re-isomerisation stage includes re-isomerising a fraction having a boiling start point of at least 200° C., which fraction is obtained by fractionation of the product obtained in the isomerisation stage, back into the isomerisation stage.

12. The solvent composition according to claim 1, wherein the content of C5 to C15 paraffins is 96 wt.-% or more, 97 wt.-% or more, 98 wt.-% or more, or 99 wt.-% or more relative to the solvent composition as a whole.

13. The solvent composition according to claim 1, wherein the paraffins comprise C5 to C10 n-paraffins.

14. The solvent composition according to claim 13, wherein the content of the C5 to C10 n-paraffins is less than 15 wt.-% of the solvent composition as a whole.

15. The solvent composition of claim 1, wherein the solvent composition has more than 57 wt.-% of the dimethylated, trimethylated or higher methylated i-paraffins relative to all of the i-paraffins in the solvent composition.

16. The solvent composition of claim 1, wherein the solvent composition has at least 62 wt.-% of the dimethylated, trimethylated or higher methylated i-paraffins relative to all of the i-paraffins in the solvent composition.

17. The solvent composition of claim 1, wherein the aniline point is 81° C. or below.

18. The solvent composition of claim 1, wherein the aniline point is 79° C. or below.

* * * * *